United States Patent [19]
Oehler et al.

[11] Patent Number: 5,141,331
[45] Date of Patent: Aug. 25, 1992

[54] ULTRASONIC TEMPERATURE MEASUREMENT AND USES IN OPTICAL SPECTROSCOPY AND CALORIMETRY

[76] Inventors: Oscar Oehler, Streulistrasse 24, 8032 Zürich; Hans Melchior, Freudenbergstr. 101 F1, 8044 Zürich, both of Switzerland

[21] Appl. No.: 432,752
[22] PCT Filed: Feb. 17, 1989
[86] PCT No.: PCT/CH89/00029
§ 371 Date: Oct. 18, 1989
§ 102(e) Date: Oct. 18, 1989
[87] PCT Pub. No.: WO89/07753
PCT Pub. Date: Aug. 24, 1989

[30] Foreign Application Priority Data

Feb. 19, 1988 [CH] Switzerland ............... 624/88
Feb. 13, 1989 [CH] Switzerland ............... 491/89

[51] Int. Cl.$^5$ ............... G01K 11/22; G01K 11/26; G01N 29/00
[52] U.S. Cl. .................. 374/118; 374/117; 374/31; 356/432; 73/657; 73/602; 73/24.01
[58] Field of Search ............ 374/31, 32, 39, 117, 374/118, 119, 34, 130, 131; 73/24.01, 24.02, 657, 602; 356/432 T

[56] References Cited

U.S. PATENT DOCUMENTS

| | | | |
|---|---|---|---|
| 3,303,340 | 2/1967 | Hewett et al. | 374/130 |
| 3,468,157 | 9/1969 | Burk et al. | 73/24.01 |
| 3,513,699 | 5/1970 | Reilly, Jr. | 374/34 |
| 3,667,297 | 6/1972 | Vondell | 73/339 |
| 3,762,197 | 10/1973 | Roof et al. | 73/24.01 |
| 4,003,242 | 1/1977 | Houben et al. | 73/24 |
| 4,175,423 | 11/1979 | Braun et al. | 73/24.01 |
| 4,215,582 | 8/1980 | Akita | 374/119 |
| 4,265,125 | 5/1981 | Mahany | 374/117 |
| 4,280,183 | 6/1981 | Santi | 73/24.01 |
| 4,317,366 | 3/1982 | Tewer et al. | 374/117 |
| 4,475,024 | 10/1984 | Tateda | 374/117 |
| 4,683,750 | 8/1987 | Kino et al. | 73/606 |
| 4,708,494 | 11/1987 | Kleinerman | 374/131 |
| 4,848,924 | 7/1989 | Nuspl et al. | 374/117 |

FOREIGN PATENT DOCUMENTS

| | | | |
|---|---|---|---|
| 3108756 | 11/1982 | Fed. Rep. of Germany. | |
| 2278073 | 2/1976 | France. | |
| 0147027 | 11/1981 | Japan | 374/119 |
| 0083625 | 4/1988 | Japan | 374/117 |

OTHER PUBLICATIONS

H. W. Grice et al.; "Performance and Applications of an Ultrasonic Detector for Gas Chromatography", *Journal of Chromatographic Science*, vol. 7, Nr. 4, pp. 239–240, (Apr. 1967).

K. Ebeling et al.; "Microcalorimeter for Measuring Heat of Straining or Destraining of Sheetlike Materials", *The American Institute of Physics* (US), vol. 45, Nr. 3, pp. 419–426, (Mar. 1974).

Primary Examiner—Allan N. Shoap
Assistant Examiner—Diego F. F. Gutierrez
Attorney, Agent, or Firm—Walter C. Farley

[57] ABSTRACT

A process and apparatus for the photothermal and/or calorimetric investigation of gaseous, liquid and solid measuring material is based on the detuning of an ultrasonic resonator (1). The latter has an ultrasonic transmitter (2) and an ultrasonic receiver (3), which face one another. The signal from the receiver is analyzed by an analyzer (5) as to its amplitude or phase position which gives, as a result of the temperature dependence of the sonic velocity, information on thermal changes in the ultrasonic resonator designed as a gas cell or calorimeter. The present apparatus makes it possible to detect gases or to calorimetrically investigate the material to be investigated, particularly light-conducting elements (5), such as light fibers.

27 Claims, 2 Drawing Sheets

ULTRASONIC TEMPERATURE MEASUREMENT AND USES IN OPTICAL SPECTROSCOPY AND CALORIMETRY

FIELD OF THE INVENTION

The invention relates to a process and to an apparatus for measuring small temperature changes in a gas, as well as the uses thereof in optical spectroscopy calorimetry.

BACKGROUND OF THE INVENTION

A large number of different temperature measuring methods exists. For example, temperatures can be measured by means of thermal expansion (liquid thermometers, bimetallic strain gauges), the temperature dependence of the electrical resistance (resistance thermometers) or the thermoelectric voltage at the interface of different metals (thermocouple). Other methods are based on electromagnetic irradiation (infrared radiometers, pyrometers). These measuring methods are very suitable for determining the temperature in the case of solids and liquids.

Apart from gas expansion measurements performed in the gas thermometer, gas temperatures are generally indirectly measured, by bringing the gas into contact with a solid or liquid thermometer. Due to the poor thermal conductivity of gases and the low thermal energy transfer from the gas to the thermometer, such temperature measurements are relatively slow.

On the basis of the ideal gas law, the temperature of an enclosed gas can be determined via its pressure. The pressure fluctuations occurring in the case of a periodic gas temperature change, can be determined in a highly sensitive manner by means of a microphone. However, due to the aforementioned low thermal conductivity of gases, the temperature changes which occur are generally very small, so that it would be necessary to operate the microphone at very low frequencies in the subhertz range. However, microphones are not very suitable for such frequencies or even for static measurements. It is therefore of interest to seek a process permitting a direct and quasi-static measurement of the gas temperature.

Numerous uses are conceivable where it is desired to measure small temperature changes in a gas. For example, in optical gas spectroscopy, it is of interest to investigate the interaction of the radiation field with a gas. On the basis of a periodic light and in particular infrared irradiation, periodic temperature fluctuations occur in the gas.

Different devices exist for measuring the light power absorbed in a gas. The greatest significance is attached to solid radiation sensors based on the photoelectric effect. Using such sensors, use is generally made of the so-called extinction method. The absorption of the material being investigated is determined as a result of the comparison of two beams, one beam passing through the material and the other passing unimpeded to the detector. However, as opposed to this indirect method, preference is often given to a direct method, which consists of directly measuring the light absorption-caused signal. As stated, it has proved very satisfactory in this connection to measure pressure fluctuations building up in a closed cell on absorbing intensity-modulated light. This so-called photoacoustic effect is characterized by a very high sensitivity. As the measurement takes place with the aid of a microphone, it is not possible to prevent acoustic interference to the measurement, and in many cases this is not acceptable.

Another possible use of a direct gas temperature measuring method is calorimetry.

Calorimetric research is carried out in the standard calorimeter in an aqueous ambient. The measuring material is either placed directly in the water, or it is immersed in the calorimeter water in a closed vessel. The latter is located in a water tank thermally separated from the environment. The calorimetric test is based on following the temperature of this calorimeter water, to which the measuring material gives off its heat which is liberated, for example, by a chemical reaction. It must be borne in mind that the temperature distribution within the calorimeter must be as homogeneous as possible and must also coincide with that of the material being analyzed. For this purpose it is advantageous to use a stirrer.

Water is suitable as the heat transfer medium from the material to the thermometer, on the one hand due to its good thermal conductivity and on the other due to the rapid attainment of a homogeneous temperature distribution by stirring. However, in certain cases it is difficult, or even impossible, to place the reactor in the water bath of a calorimeter. Therefore calorimetric measurements are often carried out in a gaseous environment, e.g., in air, or even in vacuum, the material being placed on a substrate in the form of a disk or a crucible provided with temperature sensors. Reference is made to the differential calorimeter.

Two problems occur in the case of the gas calorimeter. On the one hand it is necessary to ensure good thermal contact between the material and the substrate and on the other hand the calorimeter chamber or container must be thermally well insulated from the environment.

The construction of a gas calorimeter, such as is e.g. used for determining the melting and reaction heats, will be described on the basis of the example of a differential calorimeter. Two crucibles are placed on a disk or plate in a cavity or container. One contains the reactive, solid or liquid material and the other an inert reference material. A thermocouple is in thermal contact with the two crucibles. In order to be able to operate the calorimeter at a high constant temperature or to be able to have a linear temperature gradient (differential scanning calorimeter), the calorimeter cavity is heatable and is optionally surrounded by a thermal insulation layer for shielding external heat sources.

If a thermally initiated reaction takes place in the material being investigated, e.g. during the heating process, then a thermoelectric voltage occurs in the thermocouple at the material contact point with respect to the reference material and this gives information on the relative heating of the material being analyzed.

It is of interest in integrated optics to determine the optical losses which are caused by the light absorption in the waveguide. Such an investigation can never be carried out in an aqueous environment, because the refractive index of water modifies the light guidance and coupling conditions and would consequently falsify the measurement. It is also virtually impossible to operate the optoelectronic element in the calorimeter container of a conventional gas calorimeter, because within the same there is no space for the means for coupling in and out light. Thus, the problem arises of carrying out a calorimetric measurement in air, in which the material is neither in good thermal contact with a substrate, nor can it be thermally adequately separated from the environment. One possibility is an indirect measurement of the enthalpy of the material over the heat loss to the environment.

Such a method is used for determining the optical losses in glass. It involves placing a glass rod in the optical resonator of a high-performance laser (P=115 W) on thin filaments and determining the stationary temperature rise $\Delta T$ caused by the light passage, as well as the cooling time $\tau$ after switching off the laser. (T.C. Rich and D.A. Pinnow, Appl. Phys. Lett. 20, 264 (1972)). A fine thermocouple fitted to the glass specimen surface is used for measuring the temperature thereof. The light power $\alpha$ absorbed in the glass rod with a radius r and a thermal capacity C is calculated as:

$$\alpha = C(\pi r^2) \Delta T/\tau P \quad (1)$$

Typically in the case of a Suprasil glass rod in the optical resonator of a 115 W laser, there was a temperature rise of $\Delta T = 0.56°$ C. and on cooling a time constant $\tau = 75s$.

As a result of the process for preventing undesired heat removal, very thin thermocouple wires were used because the heat conduction of metals is higher by approximately 4 orders of magnitude than that of air. Problems are also caused by the thermal contact between the thermally poorly conducting glass rod and the thermocouple measuring point. Generally considerable effort and expenditure is required for the thermal contacting of fine specimens, e.g. if the thermocouple must be evaporated on for ensuring a good thermal contact. Furthermore, in certain cases of very fine optoelectronic components, a metallic thermal connection cannot be achieved, if e.g. the optical characteristics are disturbed by the temperature sensor.

These examples from optical spectroscopy and calorimetry are intended to show that there is an interest in directly measuring the temperature of gases.

SUMMARY OF THE INVENTION

This has led to the object of the present invention, namely of providing a process and an apparatus making it possible to directly measure gas temperatures and to use such measurements in optical spectroscopy or calorimetry.

This object is achieved by measuring the temperature-caused detuning of an ultrasonic resonator, which is formed by two facing ultrasonic transducers, one being operated as a transmitter and the other as a receiver.

The object is also achieved in the aforementioned temperature measuring process is used for temperature measurement in optical spectroscopy and calorimetry.

The physical principle of the proposed solution of the problem is based on the temperature dependence of the sonic velocity or velocity of sound. This effect is very considerable. Thus, the sonic velocity in air in the case of a temperature rise from 25° C. to 26° C. changes from 340 to 340.6 m/sec, i.e. 0.6 m/sec degrees C or approximately 0.5% per degree C of temperature change.

The sonic velocity c in a gas is calculated according to the following formula:

$$c = \sqrt{\zeta \cdot p/\delta} \quad (2)$$

in which p is the pressure, $\zeta = c_p/c_v$ the ratio of the specific heats and $\delta$ is the density of the gas.

For an ideal gas, one obtains:

$$c = \sqrt{\zeta(p_o/\delta_o)(1+\gamma T)}, \text{ in which } \gamma = 1/273.2 \ K^{-1} \quad (3)$$

The negligible pressure dependence of the sonic velocity for an ideal gas is noteworthy.

As the thermodynamic characteristics of air at room temperature do not differ significantly from those of an ideal gas, the measurement of sonic velocity variations represents a substantially pressure-independent determination of gas temperature changes.

The sonic velocity can be determined, for example, from the time delay between the emission of a pulse and the return of its echo. However, in the present case the electronic expenditure would be considerable, because as a result of the temperature dependence of the sonic velocity, the measurement of a temperature change of $\Delta T = 0.1$ mK would require a resolution of the time measurement of 5.2 ps.

Due to the high side or slope steepness in the vicinity of an acoustic resonance, or the high phase dependence in the resonance maximum, it is appropriate to determine the change in the sonic velocity via the detuning of an acoustic resonator.

It would also be conceivable to operate a transmitter continuously in acoustic resonance and to follow the impedance dependence thereof. However, it would then be necessary to deal with the problem of measuring a very small change to a large signal.

Another possibility of measuring the sonic velocity is to use two ultrasonic transducers, one being operated as the transmitter and the other as the receiver. The present invention is based on this method.

As the proposed ultrasonic measurement permits a substantially pressure-independent determination of gas temperature changes, in the case of opto-spectroscopic uses reference can be made to a so-called photothermal measurement, as opposed to the so-called photoacoustic method, in which the pressure fluctuations in the gas are determined by means of a microphone when irradiating with intensity-modulated light. The question arises as to the extent by which a photothermal measurement can lead to advantages compared with a photoacoustic measurement of gases.

Obviating acoustic interference is clearly advantageous. Our own measurements comparing photoacoustic and photothermal methods have clearly shown a difference between them. Whereas the photoacoustic effect disappears if the cell is not completely closed in the case of low frequency operation, no significant dependence of the opening state of the cell was established in the case of the photothermal signal measured by mans of ultrasonics. In this connection reference is made to the following article by O. Oehler, J. Wieland and S. Friedrich "Measurement of small temperature variations in a gas by ultrasonics", Helv. Phys. Acta, 61, 885 (1988) and also "Ultrasonic device for detection of IR radiation absorbed in a gas", Proc., of the Int. Conf. on Infrared Phys., Zurich, 1988.

Thus, the photothermal method offers advantages compared with the photoacoustic method where large pressure fluctuations occur. However, it is pointed out that in the closed call the photoacoustic method has a sensitivity improved by approximately a factor of 50.

Further reference will now be made to the use or application indicated in the set problem, namely calorimetry.

As stated, conventional calorimetric methods require a good thermal contacting of the material to be investigated. In the present case the thermodynamic quantities are directly determined from the temperature gradient of the air surrounding said material.

For determining the enthalpy of the material, it is also necessary according to formula (1) to know the stationary temperature rise $\Delta T$ thereof. This determination can be obviated by a calibration measurement on a reference specimen.

However, the reliability of such a calibration presupposes that it is possible to measure the giving off of heat from the material to be to the surrounding air and that of the reference specimen to the environment. A problem would be encountered if the surface characteristics had a significant influence on the heat abstraction, such as is the case with heat radiation. However, as in the present case there are only very small temperature rises $\Delta T$, measurement takes place at a relatively low temperature and the dimensions of the measuring cell are small, the radiation proportion of the heat flow compared with the convective proportion can be ignored. However, this means that in a first approximation the heat given off is only dependent on the geometry of the sample of material or the reference specimen.

The ultrasonic method makes it possible to measure the temperature of the gas surrounding the material to be analyzed and without causing local interference by using leads. It is merely necessary for the specimen being analyzed and the reference specimen to be in a comparable ultrasonic field.

This method has a similarity with those used for measuring the optical absorption of thallium halides. In the latter case the optical losses are photoacoustically determined, in that the material is brought into a closed chamber and the pressure changes caused by light absorption are measured by means of a microphone (P. Horn, A. Schmid and P. Braunligh, Jour. Quantum Electr., QE 19, 1169 (1983)). As opposed to these photoacoustic measurements the ultrasonic method permits a local determination of temperature differences, while photoacoustically all the heat released in the closed cavity is measured. Thus, when using ultrasonics, it is easier to eliminate marginal effects. In addition, the photoacoustic method requires a high sealing level of the calorimeter container, particularly when working at very low frequencies. When using the ultrasonic method, it is merely necessary to ensure that external gas flows have no influence on the calorimeter container.

BRIEF DESCRIPTION OF THE DRAWINGS

The invention is described hereinafter relative to the following drawings, wherein.

DESCRIPTION OF THE PREFERRED EMBODIMENTS

Figure 1:
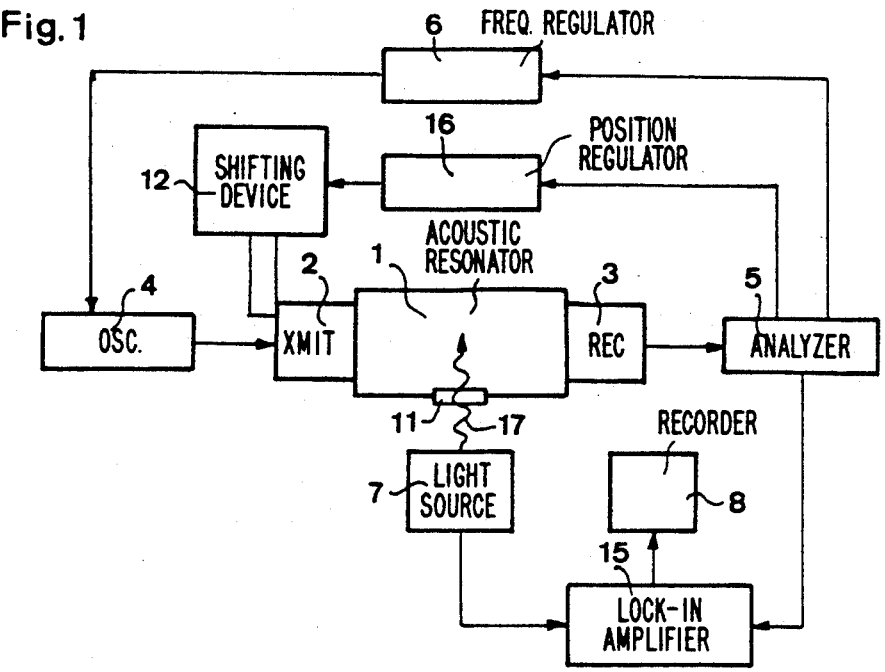
FIG. 1 is a general block diagram of an ultrasonic resonator for measuring temperature fluctuations caused by light absorption in a gas.

FIG. 1 shows the construction of the aforementioned ultrasonic means for measuring small temperature fluctuations in a gas caused by infrared radiation absorption. The gas temperature measuring method is based on the large temperature dependence of the sonic velocity of gases. The latter is measured by means of an ultrasonic field, mainly in the form of an acoustic resonator 1. The acoustic resonance builds up between the ultrasonic transducer pair comprising an ultrasonic transmitter 2 and an ultrasonic receiver 3.

The ultrasonic transmitter 2 is excited by generator 4 at a frequency of typically several hundred kHz. The generator signal can be sinusoidal or can comprise a regular train of e.g. rectangular pulses. At receiver 3 appears a signal, whose peak-to-peak value is dependent on the tuning of resonator 1, apart from the sensitivity of receiver 3 and the sound absorption in resonator chamber 1. The receiver signal is supplied to a device 5, referred to hereinafter as the analyzer. This device 5 either analyses the peak-to-peak value of the signal received, or it determines the phase position of the signal with respect to the input signal at transmitter 2. This analysis of the signal supplied by receiving 3 is e.g. based on a peak-to-peak measurement, a rectification with following smoothing, a phase detection or a phase-sensitive amplification by means of a lock-in amplifier.

By the choice of the frequency and the length of the resonator in the case of a peak-to-peak analysis, it is appropriate to operate the ultrasonic resonator in one resonance flank. In the case of phase detection, the resonator is advantageously operated in the resonance maximum, i.e. in the maximum phase change range. It is also advantageous to choose a high ultrasonic frequency due to the substantial proportionality of the peak-to-peak rise to the frequency.

The upper limit of the ultrasonic frequency is given by the sound absorption capacity of the specimen gas, which rises sharply with increasing frequency above 100 kHz. However, it is pointed out that the frequency can be made higher than is possible with commercial air-adapted ultrasonic transducers (50 to 220 kHz). Thus, in the present case the sound signal does not have to be efficiently transmitted over a distance of several meters or decimeters, such as is normally desired and instead it only has to be transmitted in the millimeter range.

By operating the ultrasonic resonator in a resonance flank in peak-to-peak analysis, or in the resonance maximum for phase detection, as well as by the choice of a high frequency, it is ensured that the temperature-caused change in the tuning has a maximum effect on the output signal of the analyzer 5.

The change to the resonator tuning can be gathered directly from the change to the signal envelope, i.e., the quasi-direct current value or phase displacement at analyzer 5. However, it is pointed out that in both cases the linear temperature measuring range is very limited. However, as only small temperature fluctuations are to be measured, this restriction is too serious. However, slow drift-like temperature changes can bring about a drift in the resonator tuning and therefore a change in the temperature sensitivity. Therefore ways must be sought for effectively counteracting large long-term effects.

For example, the ultrasonic frequency can be followed up in such a way that the resonator running, i.e., the peak-to-peak value at the receiver 3 remains constant. To this end, the output signal of analyzer 5 can be supplied as a control signal via a suitable regulator 6 to a voltage-controlled generator 4. The coverable temperature measuring range is given by the operating range of the ultrasonic transducers. Typically, with ultrasonic transducers 2, it is possible to cover desired frequency ranges of 1 to 2%.

However, a randomly large temperature range can be obtained if the resonator 1, instead of being tuned electrically, is tuned by means of a regulator 16 and a mechanical shifting device 12 by modifying the spacing between the ultrasonic transducers. However, it is pointed out that in this case the tuning is relatively complicated. In particular, the precision requirement on the mechanical construction is considerable. For example, the Q factor of the ultrasonic resonator 1 drops significantly if the surfaces of the ultrasonic transducers 2,3 are not precisely adjusted in parallel.

It is also conceivable to combine both tuning types of the ultrasonic resonator, i.e., the mechanical and electrical tuning types. This situation is shown in FIG. 1. For example, the coarse tuning can be carried out mechanically with the aid of a corresponding regulator 16 and the shifting device 12, while the fine tuning can be carried out electrically by means of regulator 6 and the voltage-controlled oscillator 4.

Conclusions can be drawn regarding the sonic velocity and therefore the temperature of the gas in the ultrasonic resonator 1 from the output signal of analyzer 5 of the output quantity. The output signal of analyzer 5 is therefore retained in a recorder 8.

Temperature variations in the ultrasonic resonator 1 can e.g., be achieved by light and, in particular, infrared irradiation 17. Small temperature fluctuations in the ultrasonic resonator 1, which are brought about by absorption of intensity modulated light radiation and consequently correlated with the light signal, can be measured, for example, by means of an analyzer 15 in the form of a lock-in amplifier. The latter uses as the reference the intensity-modulated signal of light source 7. The output signal of analyzer 15 is the sought measured value, which gives information on the light absorption in the ultrasonic resonator. This signal is therefore supplied to a recorder 8, which can be in the form of a plotter, voltmeter or computer input. The described process makes it possible to measure gas temperature changes into the range of $10^{-4}$ degrees. Further details are provided in the aforementioned articles by O. Oehler, J. Wieland and S. Fredrich.

It would initially not appear to be particularly advantageous to, on the one hand, use the output signal of analyzer 5 for further analysis in the lock-in amplifier 15 and, on the other hand, to keep this signal at a fixed value by means of regulator 6. However, the objective is to use regulator 6 for compensating slow drift phenomena, so that the lock-in amplifier 15 measures the rapid, light source-synchronous signals.

Figure 2:
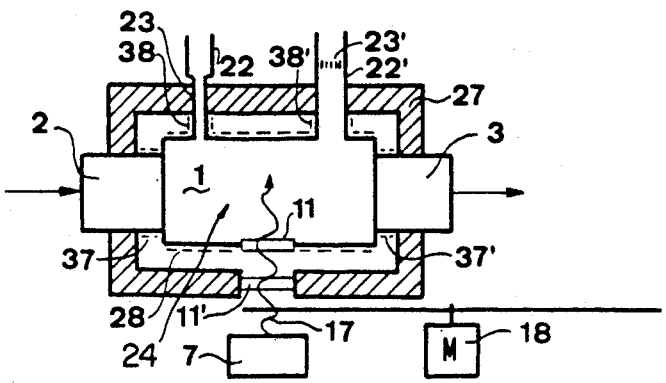
FIG. 2 is a schematic sectional view of the photothermal gas detection means with modulating and filtering means for the incident light radiation.

FIG. 2 shows a more detailed view of an apparatus for measuring the photothermal effect. The ultrasonic resonator 1 is formed by the two facing ultrasonic transducers 2,3. The light from source 7 passes through a window 11 into the ultrasonic resonator 1 constructed as a gas cell. There is at least one opening 22,22' in the gas cell wall for exchanging the gaseous material 24, being analyzed. The openings are optionally proved with flow resistances 23,23', which can be in the form of valves, pipe constrictions 23, filter plates 23', or gas-permeable membranes. It is pointed out that these flow resistances 23,23' need not have a sound absorbing effect, unlike in the case of photoacoustic measurements at low frequencies, where a good acoustic separation of the cell from the environment is unavoidable. It must merely be ensured, as stated, that external temperature fluctuations have not effect on the ultrasonic resonator 1. There would be no need for light entrance window 11, if it can be ensured that the opening in the ultrasonic resonator leads to no significant gas circulation-caused temperature fluctuations.

Figure 3:
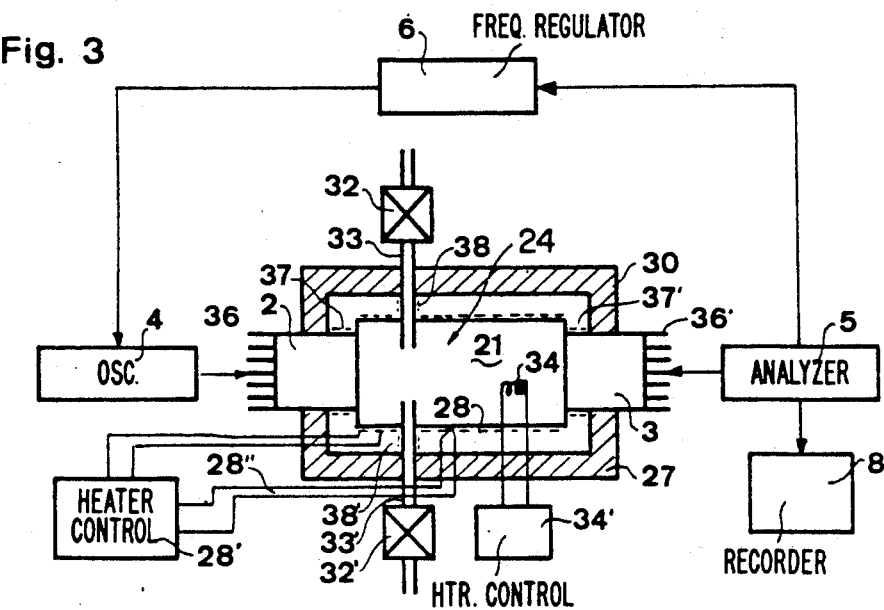
FIG. 3 is a schematic sectional view of gas calorimeter, based on an ultrasonic resonator and suitable for a fluid measuring material.

For preventing undesired temperature fluctuations in the ultrasonic resonator 1, it is recommended that it be surrounded by a jacket-like thermal insulation 27 and/or optionally kept at a constant temperature by means of a heating device 28, a heating control device 28' and a heat sensor 28" (FIG. 3). It can also be advantageous to bring the gaseous material to the ultrasonic resonator temperature by heating the feed lines with heating elements 38,38'.

The light source 7 is intensity-modulated, which is e.g., achieved by switching the current on and off, or by means of a light chopper 18 (FIG. 2), located in light beam 17 between light source 7 and ultrasonic resonator 1. An optical filter 11' can also be positioned in the light beam 17. The insertion of such a filter is particularly appropriate if the source 7 has a broad-band spectrum, i.e., if for example the light source 7 is a heat emitter. In this case an optical band-pass filter 11' can produce adequately monochromatic radiation, so that a selective light absorption by gases in the cell is ensured.

If the wavelength of the light entering the ultrasonic resonator 1 through window 11 is in a spectral range where there is a selective absorption by gases, the apparatus shown in FIGS. 1 and 2 can be used for selective detection of gases. However, the sensitivity is not as high as with an apparatus based on the photoacoustic effect, but the apparatus has a negligible fault susceptibility to pressure fluctuations and solid-borne sound.

FIG. 3 shows an embodiment of a calorimeter based on an ultrasonic resonator 1. Similar to the apparatus shown in FIG. 1, the local temperature of a gas, can be the measuring specimen or a fluid measuring specimen. Unlike the apparatus of FIG. 1 the absorption of light does not lead to a change in the gas temperature but instead affects the thermal behavior of the measuring material, e.g., a chemical reaction in a gas, an aerosol or a liquid brought into the resonator 1. The calorimeter 30 once again comprises the two ultrasonic transducers 2,3 which face one another and laterally bound the ultrasonic resonator 1.

The ultrasonic transducer used as the transmitter 2 is connected to an oscillator 4 and is excited by the latter. The receiver 3 emits an output signal to analyzer 5 and is evaluated there on the basis of a peak-to-peak or phase analysis. The tuning of oscillator 4 is readjusted by means of regulator 6. With regards to the operation of the temperature measuring method, reference should be made to the description of FIG. 1.

It is important for the accuracy of this measuring method that the local temperature distribution in the area around the material 24 is not disturbed by external influences. This can on the one hand be achieved in that the calorimeter container is largely sealed off and is consequently not under the influence of external air flows and on the other hand it must be ensured that the calorimeter inner walls have a constant, uniform temperature. This makes it possible to avoid undesired convection flows within the calorimeter. It is advantageous for this purpose to surround the ultrasonic resonator 1 and ultrasonic transducers 2,3 with a jacket-like thermal insulation 27.

It is also appropriate to provide the ultrasonic resonator 1 with a thermostatically controlled heating means 28. Like the apparatus of FIG. 2, means 28 regulates the temperature of resonator 1 by means of the heating control device 28' and heat sensor 28''.

Ultrasonic transmitter 2 is a decisive heat source. In order to obtain stationary thermal conditions, it is appropriate to provide the ultrasonic transducers 2,3 particularly the transmitter 2, with cooling means 26,26' e.g., in the form of cooling fins or Peltier elements. As the impedance of the ultrasonic transducers 2,3, is somewhat dependent on the operating frequency, an impedance minimum occurring at resonance, the thermal loading of transducers 2,3, is also variable as a function of changes in the operating frequency. In order to ensure a uniform ultrasonic transducer temperature, it is consequently advantageous to heat same by means of heating elements 37,37' in such a way that the heat supply to transducers 2,3, is constant. In analogy to the heating means 28 of ultrasonic resonator 1, this can take place by means of a heating control device and heat sensors.

The gaseous or liquid field to be investigated is e.g. introduced by means of valves 32,32' and feed lines 33,33' into the reaction zone 31 of ultrasonic resonator 1. In order to prevent a heat supply via the fluid, the latter is optionally brought, by means of heating elements 38,38' fitted to feed lines 33,33', to a temperature prevailing in the ultrasonic resonator 1 beforehand.

It is pointed out the calibration of the calorimeter is very important, because the temperature of the material 24 is not directly determined. This function is e.g. fulfilled by a heating element 34, which is operated by means of a feed device 34'.

It is pointed out that the calorimetric investigation of gases and aerosols by means of the described apparatus represents an exception, because the sonic velocity is not only dependent on the gas temperature, but also on the gas type. Thus, not only the temperature of the gas reaction, but also the gas composition in the reactor chamber is measured.

Figure 4:
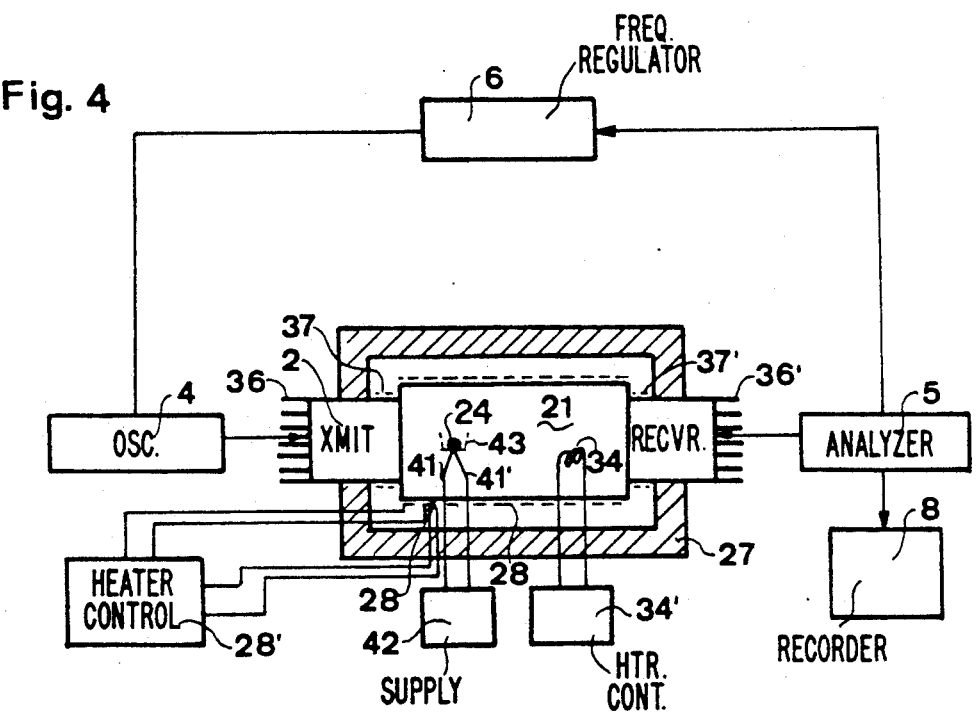
FIG. 4 is a schematic sectional view corresponding gas calorimeter for a solid or liquid measuring material.

FIG. 4 shows a calorimeter suitable for tests on solids and liquids. The apparatus consequently has a similar field of use to the aforementioned differential scanning calorimeter. However, unlike in the case of the latter, the temperature of the material 1 is not directly determined and instead that of the surrounding gas is determined.

The construction of the apparatus is very similar to that described in conjunction with FIG. 3. However, the measuring material is not introduced directly into the ultrasonic resonator via feed lines 33, 33' and is instead fixed mechanically within resonator 1. Compared with the differential calorimeter, the fixed material 24 is not introduced into a crucible 43 and can instead be directly fixed, e.g. by thin mounting supports 41,41' in the ultrasonic resonator. These mounting supports can e.g. be electric leads, which initiate the reaction in the measuring material 24.

Liquids can e.g. be introduced into the ultrasonic resonator 1 from a supply 42 by means of thin capillaries, which simultaneously fulfill the function of the mounting supports 41,41'. The liquid material to be investigated can either be present on the capillary tips, or can be filled into a small cup 43.

The remaining calorimeter components, such as the reference heating element 34, the heating means 28,37,37' of ultrasonic resonator 1, or the ultrasonic transducers 2,3, the cooling means 36,36' of the ultrasonic traducers and the thermally insulating jacket 27 of the calorimeter have been described hereinbefore.

Figure 5:
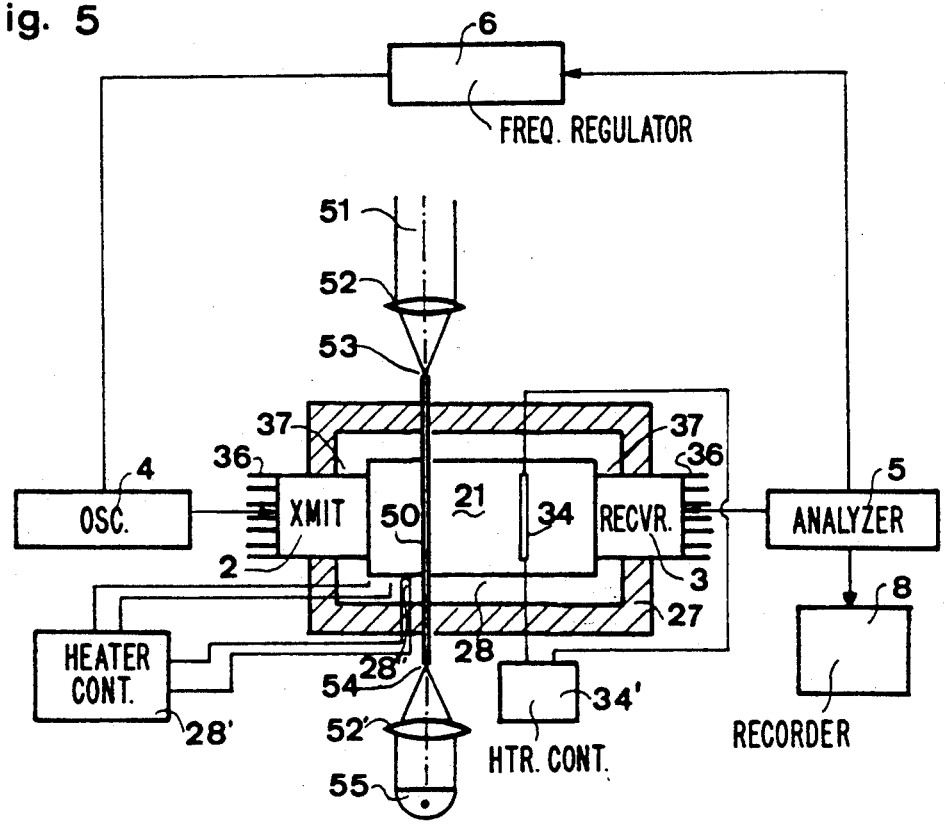
FIG. 5 is a similar view of a calorimeter for testing light guides and integrated optical elements.

FIG. 5 shows a calorimeter for investigating optical components. A considerable interest exists for calorimetric measurements on integrated-optical and optoelectronic components, such as light-conducting fibers, integrated optical light emitters, light receivers, optoelectronic light switches and connecting points between optical components. Only by means of thermal investigations, is it possible to differentiate the light absorption occurring in the optical material from undesired light dispersion and light coupling out. The absorbed light power is converted into calorimetrically measurable heat, while the undesired, coupled out light does not appear calorimetrically. An optimization of the optical components requires precise knowledge of the origin of the losses. Therefore the optical losses in optical materials and components, such as glass, are frequently calorimetrically measured. Thus, as stated, the optical loss in glass is determined by placing a glass rod int he optical resonator of a high-performance laser and measuring the specimen temperature rise during laser operation, as well as the time constant of the temperature reduction after switching off the laser (T.C. Rich and D.A. Pinnow, Appl. Phys. Lett. 20, 264 (1972)). As mentioned hereinbefore, the optical absorption of thallium halides is photoacoustically determined, in that the measuring material is brought into a closed chamber and the pressure changes caused by light absorption measured by means of a microphone (P. Horn, A. Schmid and P. Braunlich, Jour. Quantum Electr., QE 19, 1169 (1983)).

As has already been stated, calorimetric measurements on optical components cannot be performed during operation in water. The aqueous ambient would significantly change or render impossible light guidance, due to the refractive index of water. It is therefore necessary to perform the measurements in a gas calorimeter. When using a conventional differential calorimeter considerable technical difficulties are encountered in solving the problem of coupling in light and creating a good thermal contact between the specimen and the solid temperature sensor. Thermocouples could be applied to the material to be analyzed, e.g. by evaporating on, but the costs would be considerable.

In the apparatus according to FIG. 5 the light beam 51 is coupled into the optically conducting material 50 outside the calorimeter container 1 by means of the focusing optics 52 in the coupling in zone 53. The light coupled out of the optical element 50 in area 54 on the opposite side of resonator 1 is optionally supplied following further focussing by means of optics 52' to a light detector 55. The optical loss can be determined by means of the signal at said light detector 55.

The remaining components of the calorimeter have already been described in detail in conjunction with FIGS. 3, 4, and 5, so that no further reference will be made thereto. The calorimetric measurement is either performed in that the gas temperature in the environment of the optically conducting element 50 is measured before and after switching on the optical light coupling in, or in that the light is alternately coupled into the measuring material 50 at very low frequency.

It has hitherto been assumed that there is light in the calorimeter chamber. However, it is also conceivable to use another gas. In particular a gas with good thermal conductivity, such as hydrogen or helium, would lead to the advantage of a small cooling time constant. Thus, e.g. the modulating frequency could be increased in the alternating operation of the calorimeter.

We claim:

1. A method of investigating a material in a gaseous environment comprising the steps of
   immersing the material in a gaseous environment in the ultrasonic field of a tunable ultrasonic resonator,
   exchanging energy with the material,
   tuning the resonator to a desired operating location on a resonance curve, and
   measuring the amount of detuning of the ultrasonic resonator as a measure of the temperature-dependent change of the ultrasonic field resulting from the heat absorbed by or given off by the material from or to the gaseous environment, a characteristic of the material being determined from the amount of detuning of the ultrasonic resonator.

2. A method according to claim 1 and including forming the ultrasonic resonator with two ultrasonic transducers facing each other, and operating one of the transducers as a transmitter and the other transducer as a receiver.

3. A method according to claim 2 and including tuning the resonator to an operating location on a flank of the resonance curve, and measuring the detuning of the resonator by measuring the amplitude change in the resonator output.

4. A method according to claim 2 and including operating the resonator close to the peak of the resonance curve, and measuring the detuning of the resonator by measuring the phase change between the transmitted and received ultrasonic energy in the resonator.

5. A method according to claim 2 and including controlling the tuning of the resonator using a feedback regulator.

6. A method according to claim 1 wherein the material being investigated is gaseous, and the investigation performed comprises photothermal gas analysis wherein the step of exchanging energy includes radiating light onto the material being investigated in the ultrasonic field.

7. A method according to claim 6 and including intensity-modulating the irradiating light.

8. A method according to claim 7 wherein the light is monochromatic.

9. A method according to claim 8 and including providing means for exchanging the gaseous material to be measured.

10. A method according to claim 1 wherein the investigation performed is a calorimetric investigation and includes providing an independent heat source in the ultrasonic field, and using the heat source as a reference.

11. A method according to claim 10 wherein the material to be measured is a fluid and including delivering the material to be measured by at least one feed line into the ultrasonic field during the calorimetric measurement.

12. A method according to claim 10 wherein the material to be measured is a solid and is fixedly mounted in the ultrasonic field.

13. A method according to claim 1 wherein the material to be measured is electrically conductive and including supplying electrical energy thereto.

14. An apparatus for investigating a material in a gaseous environment comprising the combination of
   a calorimeter container;
   means for receiving a material to be investigated in said container;
   means for adding energy to, or extracting energy from, said material to be investigated;
   temperature measuring means for measuring the heat given off from or absorbed by the material to be measured, said temperature measuring means comprising
   first and second ultrasonic transducers having active surfaces for respectively transmitting and receiving ultrasonic energy,
   means for mounting said transducers on opposite sides of said container with said active surfaces facing each other in spaced relationship so that said transducers form a tuned ultrasonic resonator,
   means for delivering energy to said first transducer to operate said transducer as the transmitter portion of said resonator, and
   analyzer means connected to said second transducer operating as a receiver for measuring detuning thereof as a result of temperature changes and as a measure of temperature changes in said container.

15. An apparatus according to claim 14 wherein said analyzer means measures amplitude changes of the received ultrasonic signal as a measure of temperature changes.

16. An apparatus according to claim 14 wherein said analyzer means measures phase changes of the received ultrasonic signal with respect to the signal applied to the ultrasonic transmitter as a measure of temperature changes.

17. An apparatus according to claim 14 wherein said means for delivering energy is an oscillator, and further comprising regulator means connected to an output of said analyzer and to an input of said oscillator for controlling oscillator frequency, and means for altering the spaced relationship between said transducers in accordance with said analyzer output to tune said acoustic resonator.

18. An apparatus according to claim 14 wherein said calorimeter container includes a window and means for exchanging gases within said container.

19. An apparatus according to claim 18 wherein the material is light-conducting and further comprising a light source for supplying energy to the material in said resonator in the form of a beam of light, chopper means for repetitively interrupting said beam of light between said source and said resonator, and an optical filter in said light beam.

20. An apparatus according to claim 19 wherein said container includes means defining at least one opening into said container, said opening including flow resistance means for inhibiting gas flow therethrough.

21. An apparatus according to claim 14 and further comprising a reference heating element in said container between said transducers, and means for supplying energy to said heating element.

22. An apparatus according to claim 14 and including feed line means for introducing into said container the material to be investigated in a fluid form.

23. An apparatus according to claim 14 and including means for holding said material to be investigated in a fixed location within said ultrasonic resonator, wherein said material is a liquid or a solid.

24. An apparatus according to claim 23 wherein said material to be investigated is a light-conducting material, the apparatus further comprising optical focussing means for coupling light into said material to be measured.

25. An apparatus according to claim 14 and further comprising means including a heating element for establishing and maintaining the temperature of said container at a predetermined level, said means including a temperature sensor and a control device for said heater.

26. An apparatus according to claim 14 and further comprising temperature control means for establishing and maintaining at least one of said transducers at a predetermined temperature.

27. An apparatus according to claim 14 and including means for selectively detecting gases.

* * * * *